United States Patent [19]

Hashimoto

[11] Patent Number: 5,079,868
[45] Date of Patent: Jan. 14, 1992

[54] PLANT TREATMENT WITH UREA PEROXIDE

[75] Inventor: Saburo Hashimoto, Yorba Linda, Calif.

[73] Assignee: Union Oil Company of California, Los Angeles, Calif.

[21] Appl. No.: 543,324

[22] Filed: Jun. 25, 1990

[51] Int. Cl.⁵ ............................................... C09K 3/18
[52] U.S. Cl. ............................................ 47/2; 252/70
[58] Field of Search ............................................... 47/2

[56] References Cited

U.S. PATENT DOCUMENTS

| | | | |
|---|---|---|---|
| 3,912,490 | 10/1975 | Boghosian . | |
| 3,933,577 | 1/1976 | Penque | 71/14 |
| 4,013,440 | 3/1977 | Vale | 71/21 |
| 4,344,979 | 8/1982 | Gago et al. . | |
| 4,375,734 | 3/1983 | Kozloff et al. | 47/2 |
| 4,484,409 | 11/1984 | Caple et al. | 47/2 |
| 4,834,899 | 5/1989 | Klevecz | 47/2 |
| 4,855,230 | 8/1989 | Lindow | 47/2 |
| 4,863,445 | 9/1989 | Mayhan et al. | 604/317 |

OTHER PUBLICATIONS

S. E. Lindow, D. C. Arny, C. D. Upper, "The Role of Bacterial Ice Nuclei in Frost Injury to Sensitive Plants," *Plant Cold Hardiness and Freezing Stress*, Academic Press, Inc., 1978, pp. 249-250.

L. L. Kinkel and J. H. Andrews, "Disinfestation of Living Leaves by Hydrogen Peroxide," *Trans. Br. mycol. Soc.* 91 (3), (1988), printed in Great Britain, pp. 523-528.

James H. Bryce, Dennis D. Focht, and Lewis H. Stolzy, "Soil Aeration and Plant Growth Response to Urea Peroxide Fertilization,"*Soil Science*, vol. 134, No. 2, Aug. 1982, pp. 111-116.

Primary Examiner—Richard E. Chilcot, Jr.
Assistant Examiner—Joanne C. Downs
Attorney, Agent, or Firm—Gregory F. Wirzbicki; William M. Dooley

[57] ABSTRACT

Compositions comprising urea peroxide are effective for treating plants for fungal, bacterial, and viral infections and for infestations of mites and insects. The compositions reduce populations of ice nucleating bacteria on plants, thus protecting the plants from frost damage. The compositions are applied to the aerial portions of plants, e.g., leaves, flowers, fruits, stems, branches, vines, and trunks.

29 Claims, No Drawings

PLANT TREATMENT WITH UREA PEROXIDE

FIELD OF THE INVENTION

This invention relates to agricultural pesticides, e.g., fungicides and bactericides, and to compositions that protect plants, trees, and vines from frost damage.

INTRODUCTION

Fungi, bacteria, viruses, mites, insects, and other pests are major causes of plant damage and crop loss.

Frost also causes serious damage and crop loss. Many plants can survive temperatures a little below 0° C., e.g., down to about −5° or −10° C., without serious damage, as long as no ice forms on the plants. Often, however, ice does form at such temperatures and plants suffer frost damage. For ice to form at such temperatures, heterogeneous ice nuclei must be present to initiate crystallization of supercooled water. When fewer ice nuclei are present, less ice forms and less damage occurs to the plants. Bacteria present on the plants play a role in frost damage by acting as ice nuclei. Two species of bacteria that have been associated with ice nucleation and frost damage to plants are *Pseudomonas syringae* and *Erwinia herbicola*.

SUMMARY OF THE INVENTION

It has now been found that urea peroxide is effective for inhibiting or destroying plant pests, such as fungi, bacteria, viruses, mites, and insects, when applied to aerial portions of plants. Frost protection is obtained through destruction of ice nucleating bacteria.

DETAILED DESCRIPTION OF THE INVENTION

Urea peroxide comprises one or more adducts of urea and hydrogen peroxide. It can be made by crystallization from an aqueous solution of urea and hydrogen peroxide and is available commercially from a number of sources. The most common form of urea peroxide is the 1:1 molar adduct of urea and hydrogen peroxide. Adducts having 2 and 4 moles of hydrogen peroxide per mole of urea have been reported and can be used. The 1:1 adduct is preferred for use in the practice of this invention. Mixtures of the various adducts can also be used.

Solid urea peroxide and solutions thereof are preferably stabilized by the addition of a stabilizer. Suitable stabilizers are described in U.S. Pat. Nos. 3,629,331, 3,912,490, and 4,155,738, all of which are incorporated herein by reference.

Urea peroxide can be applied directly to the aerial portions of plants, i.e., any portion of the plant above the soil or growing medium, such as leaves, flowers, fruits, branches, stems, vines, crowns, and trunks. Urea peroxide is believed to act directly upon the pest to be controlled and is therefore preferably applied to the vicinity occupied by the pest.

Urea peroxide can be formulated for application in ways similar to those used for other topical plant treatments. The urea peroxide can be applied in solid form, e.p., as a dust, usually in combination with a solid carrier/diluent such as clay, talc, or the like; or as a suspension in a nonsolvent liquid carrier such as a light oil.

Urea peroxide can also be formulated and applied in solution. It is believed that urea peroxide, i.e., the urea-hydrogen peroxide adduct, dissociates to some extent in certain solvents, e.g., water, with the extent of dissociation being inversely related to the concentration of the solution. Furthermore, it is known that urea peroxide can be prepared by crystallization from a solution of urea in concentrated hydrogen peroxide. When a solution containing urea and hydrogen peroxide in a volatile solvent such as water is applied to a plant, for example by sprayinq, the solvent will normally evaporate quickly. This results in progressively higher concentrations of urea and hydrogen peroxide in the remaining solvent until at some point the urea-hydrogen peroxide adduct can form. Therefore, the term "composition comprising urea peroxide" as used herein with reference to solutions refers both (a) to solutions in which at least a portion of the urea-hydrogen peroxide adduct remains intact and (b) to solutions containing urea and hydrogen peroxide. Solutions used in the practice of this invention are preferably made by dissolving urea peroxide in the chosen solvent. Less preferably, the solutions can be made by dissolving urea and hydrogen peroxide in the solvent, by dissolving either component in a solution of the other, or by mixing separate solutions of urea and hydrogen peroxide. Mixtures of solvents can also be used.

The urea peroxide adduct crystallizes in definite molar ratios of urea to hydrogen peroxide, most commonly 1:1, although 1:2 and 1:4 adducts have also been reported. Compositions having different ratios of urea to hydrogen peroxide can be prepared by adding additional urea or hydrogen peroxide to a composition comprising an adduct, by mixing adducts of different ratios, or by dissolving varying proportions of urea and hydrogen peroxide in a solvent. Beneficial results can be obtained with compositions having molar ratios of urea to hydrogen peroxide ranging from about 1:50 to about 50:1. Preferably, the ratio is between about 1:25 and 25:1, more preferably between about 1:10 and 10:1, and even more preferably between about 1:5 and 5:1. A molar ratio of 1:1 is most preferred.

Compositions of the invention are low in biuret, a phytotoxic chemical often occurring as a byproduct in the manufacture of urea. Preferably, the biuret content is less than about 2 percent, more preferably less than about 1 percent, based on the weight of urea peroxide. Most preferably, the compositions are essentially biuret-free.

A wide variety of fungal and bacterial plant pests can be controlled in accordance with this invention. For example, *Phytoohthora* species such as *p. parasitica*, *P. citroohthora*, and *P. cinnamomi*, alone with others of the family Pythiaceae and the order Peronosporales, are a major group of fungal pathogens on a wide variety of crops. Three different types of diseases are caused by this species: foliar, flower, and fruit diseases; systemic stem, crown, and root diseases; and local diseases on roots, hypocotyl, or crown. Some of the diseases are devastating, and the costs for the chemical control of these pests represent about one-third of the total fungicide market. Other genera of common fungal tests include Pythium, Monilinia, the powdery and downy mildews, rusts, and smuts.

In accordance with this invention, plants can be protected from frost damage by treating the aerial portions thereof, particularly tender portions such as leaves, flowers, fruits, and soft stems, with urea peroxide so as to reduce the population of, or inhibit the growth of, ice nucleating organisms, e.g., bacteria, thereon. This invention provides the greatest protection from frost damage under those circumstances where ice nucleating organisms are a significant factor in the occurrence of frost damage, i.e., at temperatures between about 0° and about −10° C., preferably between about 0° and −5° C. At higher temperatures, of course, ice does not form. At lower temperatures, ice can form whether ice nucleating organisms are present or not. In addition, plants vary in their hardiness to cold and freezing. Thus, the embodiments of this invention directed to frost protection are of the greatest value in the treatment of plants susceptible to damage from icing at temperatures down to about −10° C., preferably down to about −5° C.

Usually, plants are treated in anticipation of freezing temperatures, e.g., when frost-inducing conditions are predicted by a weather forecasting agency, since the ice nucleating organisms will slowly reestablish themselves after the plants are treated. Desirably, plants are treated no more than 2 weeks before frost-inducing conditions occur, perferably no more than 1 week before, and more preferably no more than 2 days before. Emergency treatment can be made at any time before ice has formed on the plants, even during the night when a frost advisory has been issued.

Both healthy plants and those which are already infected or infested with a pest can be treated in accordance with this invention. For example, healthy plants having otherwise-harmless (i.e., non-pathogenic) ice nucleating bacteria on their foliage can be treated for frost protection.

All plant varieties, including fruiting and principally vegetative varieties, can be treated in accordance with this invention. Fruiting plants, for purposes of this invention, include plants that bear any variety of produce other than vegetative growth, such as annual and perennial vegetables, fruits, nuts, grains, fiber crops, and the flowering plants. Plants grown primarily for their vegetative productivity, such as wood cross and the wide variety of grasses grown for animal feeds and decorative purposes, can also be treated in accordance with the methods of this invention.

All varieties of vegetables can be treated, including lettuce, broccoli, cauliflower, asparatus, onions, cabbages, celery, rhubarb, artichokes, tuberous crops such as potatoes, turnips, rutabagas, sugar beets, and peanuts, tomatoes, beans, bell peppers, chili peppers, eggplants, okra, etc. Illustrative of fruits that can be treated in accordance with this invention are peaches, apples, citrus, avocados, cherries, grapes (varietal and table), strawberries, raspberries, bananas, etc. Treatable nut crops include walnuts, pecans, almonds, cashews, etc. Essentially all grains can be treated, including corn, wheat, sorphum, maize, rice, barley, oats, etc. Illustrative animal feed crops and grasses include alfalfa, bermuda, rye, and bluegrass. Illustrative fiber cross include cotton, hemp, kenaf, and flax. All wood crops can be treated in accordance with this invention, including both hardwoods and conifers, such as oak, elm, maple, walnut, spruce, hemlock, alder, loblolly pine, redwood, mahogany, cypress, cedar, Douglas fir, and white pine. Flowering plants that can be treated include all varieties of domestic and commercially grown flowers, such as orchids, roses, chrysanthemums, azaleas, camellias, carnations, pansies, snapdragons, etc.

Urea perooxide compositions can be applied at a broad range of rates, depending on the plant being treated, the pest to be controlled, temperature, humidity, the concentration of urea peroxide in the composition, and the like. In general the compositions are applied at a rate of at least about 0.1 pounds urea peroxide equivalent per acre, usually at least about 1 pound, preferably at least about 5 pounds, and more preferably at least about 10 pounds per acre, Useful application rates can exceed about 1000 pounds urea peroxide per acre. Preferably, application rates are less than about 500 pounds per acre, more preferably less than about 250 pounds per acre, and most preferably less than about 150 pounds per acre.

An aqueous solution suitable for spraying can contain, for example, at least about 1 pound, preferably at least about 5 pounds, more preferably at least about 7.5 pounds of urea peroxide per 100 gallons of water; usually, the solutions contain less than about 100 pounds of urea peroxide per 100 gallons of water, preferably less than about 50 pounds, and more preferably no more than about 30 pounds per hundred gallons of water.

Spray volumes in the range of about 5 to about 200 gallons per acre are sufficient to afford adequate coverage and spray distribution for essentially all plant types except large shrubs and trees, for which volumes in that range of about 400 to about 1000 gallons per acre can be required. Spray volumes of about 5 to about 100 gallons per acre are usually adequate for most agricultural cross, and spray volumes of about 10 to about 60 gallons per acre are suitable for the treatment of row crops and nursery plants.

Urea peroxide is quite soluble in water, and solutions containing several hundred pounds per hundred gallons of water can be prepared. Such concentrated solutions may be too strong to apply directly to foliage but can be applied to the woody portions of plants, such as the trunks and branches of trees and shrubs, when strong pesticidal, e.g., fungicidal or bactericidal, activity is desired.

Solutions for spraying can also contain a suitable surfactant or wetting agent to enhance coverage. Any conventional surfactant that will not degrade or be degraded by urea peroxide can be used, such as Triton X-77 from Rohm and Haas. Surfactants can be used in concentrations ranging from about 0.01 to about 10 percent, typically from about 0.1 to about 5 percent, preferably from about 0.2 to about 4 percent.

In one embodiment of the invention, for example, an aqueous solution containing about 7.5 to about 30 pounds of urea peroxide per 100 gallons of water can be applied to citrus trees at a rate of about 400 to about 1000 gallons per acre for frost protection.

In another embodiment of the invention, an aqueous solution containing about 10 to about 20 pounds of urea peroxide per 100 gallons of water can be applied to strawberries at a rate of 50 to 100 gallons per acre for frost protection.

In another embodiment of the invention, tomato plants can be dusted with a solid composition containing urea peroxide at a rate of about 10 to about 60 pounds, e.g., 50 pounds, of urea peroxide per acre for fungicidal treatment.

While particular embodiments of the invention have been described, it will be understood that the invention is not limited thereto, since many obvious modifications can be made. It is intended to include within this invention any such modifications as will fall within the scope of the appended claims.

I claim:

1. A method of protecting a plant from frost which comprises applying to an aerial portion of said plant, said aerial portion having an umber of ice nucleating organism thereon, sufficient urea perooxide to reduce the number of said ice nucleating organisms.

2. The method of claim 1 wherein the ice nucleating organisms comprise bacteria.

3. The method of claim 1 wherein the urea peroxide is a solid.

4. The method of claim 1 wherein the urea peroxide comprises less than about 2 percent biuret by weight.

5. The method of claim 1 wherein the urea peroxide has been dissolved in a solvent.

6. The method of claim 5 wherein the solvent is aqueous and at least about 1 pound of urea peroxide per 100 gallons of water has been dissolved therein.

7. The method of claim 6 wherein at least about 5 pounds of urea peroxide per 100 gallons of water has been dissolved in the solvent.

8. The method of claim 6 wherein at least about 7.5 pounds of urea peroxide per 100 qallons of water has been dissolved in the solvent.

9. The method of claim 8 wherein up to about 30 pounds of urea peroxide per 100 gallons of water has been dissolved in the solvent.

10. A method of protecting a plant from frost damage which comprises applying a composition comprising urea peroxide to said plant when frost-inducing conditions are predicted, said plant having ice nucleating sites thereon.

11. The method of claim 10 wherein the ice nucleating sites comprises microorganisms.

12. The method of claim 10 wherein the ice nucleating sites comprise bacteria.

13. The method of claim 10 wherein the composition comprises solid urea peroxide.

14. The method of claim 10 wherein the composition comprises dissolved urea perooxide.

15. The method of claim 10 wherein the composition comprises urea and hydrogen peroxide.

16. The method of claim 10 wherein the composition comprises an aqueous solution containing at least about 1 pound of urea perooxide per 100 gallons.

17. The method of claim 10 wherein the composition comprises an aqueous solution containing at least bout 5 pounds of urea peroixide per 100 gallons.

18. A method of protecting a plant from frost damage which comprises applying to said plant, prior to the occurrence of frost-inducing conditions, a composition comprising urea peroxide.

19. The method of claim 18 wherein frost-inducing conditions occur within 2 weeks after application of the composition.

20. The method of claim 18 wherein frost-inducing conditions occur within 10 days after application of the composition.

21. The method of claim 18 wherein frost-inducing conditions occur within 5 days after application of the composition.

22. The method of claim 18 wherein frost-inducing conditions occur within 2 days after application of the composition.

23. The method of claim 18 wherein frost-inducing conditions occur within 1 day after application of the composition.

24. The method of claim 18 wherein the composition comprises less than about 2 percent biuret by weight of urea peroxide.

25. The method of claim 18 wherein the composition comprises less than about 1 percent biuret by weight of urea peroxide.

26. The method of claim 18 wherein the composition is essentially biuret-free.

27. The method of claim 18 wherein the composition is aqueous and at least about 1 pound of urea peroxide per 100 gallons of water has been dissolved therein.

28. The method of claim 27 wherein at least about 5 pounds of urea peroxide per 100 gallons of water has been dissolved in the composition.

29. The method of claim 27 wherein between about 7.5 pounds and about 30 pounds of urea peroxide per 100 gallons of water has been dissolved in the composition.

* * * * *

UNITED STATES PATENT AND TRADEMARK OFFICE
CERTIFICATE OF CORRECTION

PATENT NO. : 5,079,868
DATED : January 14, 1992
INVENTOR(S) : Saburo Hashimoto It is certified that error appears in the above-identified patent and that said Letters Patent is hereby corrected as shown below:

Column 2, line 49, "Phytoohthora" should be -- Phytophthora --; line 50, "citroohthora" should be -- citrophthora --.

Claim 1, column 5, line 1, "an umber" should be -- a number --; line 2, "organism" should be -- organisms --; "perooxide" should be -- peroxide --.

Claim 11, column 5, line 30, "comprises" should be -- comprise --.

Claim 14, column 5, line 36, "perooxide" should be -- peroxide --.

Claim 15, column 5, line 38, "perooxide" should be -- peroxide --.

Claim 16, column 5, line 41, "perooxide" should be -- peroxide --.

Claim 17, column 6, line 2, "bout" should be -- about --; line 3, "peroixide" should be -- peroxide --.

Signed and Sealed this

Tenth Day of August, 1993

Attest:

MICHAEL K. KIRK

*Attesting Officer*     Acting Commissioner of Patents and Trademarks